United States Patent
Swogger et al.

(10) Patent No.: US 10,968,119 B2
(45) Date of Patent: Apr. 6, 2021

(54) WATER TREATMENT PROCESS

(71) Applicants: Kurt W. Swogger, Austin, TX (US); John Richard Graves, Clifton, TX (US); Phillip J. Carlberg, Austin, TX (US)

(72) Inventors: Kurt W. Swogger, Austin, TX (US); John Richard Graves, Clifton, TX (US); Phillip J. Carlberg, Austin, TX (US)

(73) Assignee: U.S. Clean Water Technologies, Austin, TX (US)

(*) Notice: Subject to any disclaimer, the term of this patent is extended or adjusted under 35 U.S.C. 154(b) by 115 days.

(21) Appl. No.: 16/553,100

(22) Filed: Aug. 27, 2019

(65) Prior Publication Data

US 2020/0062619 A1    Feb. 27, 2020

Related U.S. Application Data

(60) Provisional application No. 62/755,723, filed on Nov. 5, 2018, provisional application No. 62/723,018, filed on Aug. 27, 2018.

(51) Int. Cl.
| | | |
|---|---|---|
| *C02F 1/46* | (2006.01) |
| *C02F 1/463* | (2006.01) |
| *C02F 1/467* | (2006.01) |
| *C07C 51/487* | (2006.01) |
| *C02F 1/461* | (2006.01) |
| *C02F 101/32* | (2006.01) |

(52) U.S. Cl.
CPC ............ *C02F 1/463* (2013.01); *C02F 1/4672* (2013.01); *C02F 1/46104* (2013.01); *C07C 51/487* (2013.01); *C02F 2001/46138* (2013.01); *C02F 2101/32* (2013.01)

(58) Field of Classification Search
CPC .... C02F 1/463; C02F 1/4672; C02F 1/46104; C02F 2001/46138; C02F 2101/32; C02F 1/38; C02F 2201/46135; C02F 9/00; C02F 2001/007; C02F 1/40; C02F 1/66; C02F 2001/46142; C02F 1/465; C02F 2101/301; C07C 51/487; C07C 51/42
See application file for complete search history.

(56) References Cited

U.S. PATENT DOCUMENTS

2012/0255872 A1* 10/2012 Smith ................... C02F 11/006
                                                                 205/742

* cited by examiner

*Primary Examiner* — Arun S Phasge
(74) *Attorney, Agent, or Firm* — Stephen P. Krupp

(57) ABSTRACT

A process for removing oil and other organics, especially naphthalenic acid, is disclosed. The process involves use of electrical fields using electrodes in the device, inducing gas bubbles which force contaminants to the surface of the solutions to be skimmed off and recovered.

33 Claims, No Drawings

WATER TREATMENT PROCESS

CROSS-REFERENCE TO RELATED APPLICATIONS

This application is related to U.S. Ser. No. 14/599,379, filed Jan. 16, 2015, now U.S. Pat. No. 9,896,355, the disclosure of which is incorporated herein by reference. This application also claims priority to U.S. Ser. No. 62/723,018 filed Aug. 27, 2018 and U.S. Ser. No. 62/755,723 filed Nov. 5, 2018, the disclosures of each of which are incorporated herein by reference.

FIELD OF THE INVENTION

A water treatment device and process for use in converting an aqueous emulsion of salts of naphthalenic acid into water and naphthalenic acid using a low energy process.

BACKGROUND

The process flow to remove salts of naphthalenic acid both soluble and insoluble from aqueous solution and emulsions involves acidification and subsequent removal by a device using electromagnetic fields. The initial process stream is adjusted to pH less than 7. The pH adjusted initial process stream can optionally flow to a decanting device that separates insoluble naphthalenic acid from the remainder of the initial process stream. The process stream is then flowed to a device that causes separation or oxidation of the naphthalenic acid or its salts. The device consists of parallel plates of titanium alternating with titanium plates coated with ruthenium oxide, iridium or combinations of ruthenium oxide and iridium oxide contained in a tank. The plates when connected to direct electric current act to create electromagnetic fields which coalesce emulsion of the acid that then can be skimmed and which creates peroxides or hydroxides or other reactive oxygen species that oxidize any soluble organics.

SUMMARY

In a first aspect, the invention is a process to recover naphthalenic acid salts from an aqueous stream comprising the steps, optionally sequential steps, of:
a) adjusting the pH of the naphthalenic salts with an aqueous diluent,
b) optionally adding a hydrocarbon diluent,
c) treating the naphthalenic soap derivative in aqueous diluent with an electrical field such that the naphthalenic acid coalesces into larger droplets and,
d) recovering the larger droplets, thereby removing at least 50% of the naphthalenic acid from the oil stream.
e) oxidizing any soluble forms of the naphthalenic salt or any other organics by hydroxy and peroxide groups or other reactive oxygen species,
f) formed by an electric field generated by use of Titanium comprising an electrode and by the use of coatings of ruthenium oxide or iridium oxide or combinations thereof applied to titanium electrodes.

Optionally, and preferably, a decanting step is inserted in a pretreatment module after step (a) in the first aspect above. After addition of the aqueous diluent stream, preferably comprising at least one acid, comprising alkaline soaps of acid oils, including Fats, Oils, Grease, ester acid oils and naphthalenic acid oil, the process stream is separated into an aqueous stream still containing the acid and an acid oil stream. The aqueous stream is then pumped to a decanting device (such as a decanter or centrifuge) to remove coagulated oil and then pumped to the electro-magnetic or electrical field generating device. The aqueous stream my optionally be heated to 150-350 F at a pressure of 100-250 psi. The resulting coagulated acid oil is then recovered.

The terms aqueous stream and aqueous diluent stream can be used interchangeably.

Step (e) can have a pH adjusted to from about 1 to about 8.

The electrical field of step (c) can generate hydrogen gas bubbles which attach to the naphthalenic acid.

The aqueous diluent stream of step (a) can have a pH of about 4 or less, preferably 3 or less, more preferably 2 or less, most preferably 1 or less.

The voltage of the electric field can be at least 1 V, 10 V. 100 V. 1 kV, or even at least 20 kV. The maximum Voltage of the electric field can be less than 50 kV, less than 30 kV, less than 10 kV, less than 1 kV, or even less than 100 V.

The average amperage of the electric field can be at least 1 amp, 50 amps, or even at least 100 amps. According to at least some embodiments, the maximum amps can be less than 200 amps, less than 100 amps, less than 50 amps, or less than 10 amps.

The naphthalenic soap can further comprise aqueous soluble organic compounds.

The soluble organic compounds can be at least 70% oxidized, preferably at least 80% oxidized, more preferably at least 90% oxidized, most preferably at least 98% oxidized.

Another embodiment of the invention is a process to produce water comprising less than 10,000 ppm naphthalenic acid, more preferably 1000 ppm, most preferably 100 ppm from a naphthalenic acid-containing emulsion stream comprising the sequential steps of:
a) adjusting the pH of the naphthalenic salt with a first aqueous diluent,
b) optionally adding a hydrocarbon diluent,
c) treating the naphthalenic salt in aqueous diluent with an electrical field such that the naphthalenic acid coalesces into larger droplets and,
d) recovering the larger droplets, thereby removing at least 50% of the naphthalenic acid from the oil stream. Optionally, and preferably, a decanting step is inserted in a pretreatment module after step (a) in the first aspect above. After addition of the aqueous diluent stream, preferably comprising at least one acid, comprising alkaline soaps of acid oils, including Fats, Oils, Grease, ester acid oils and naphthalenic acid oil, the process stream is separated into an aqueous stream still containing the acid and an acid oil stream. The aqueous stream is then pumped to a decanting device (such as a decanter or centrifuge) to remove coagulated oil and then pumped to the electro-magnetic or electrical field generating device. The resulting coagulated acid oil is then recovered. The first aqueous diluent stream of step (a) can have a pH of about 4 or less, preferably 3 or less, more preferably 2 or less, most preferably 1 or less. The aqueous diluent of step (a) can be a mineral acid such as sulfuric acid, hydrochloric acid and the like.

The electrical field of step (c) can generate hydrogen gas bubbles which attach to the naphthalenic acid.

The voltage of the electric field can be at least 1V, 1 OV, 100V, 1 kV, or even at least 20 kV. The maximum Voltage of the electric field can be less than 50 kV, less than 30 kV, less than 10 kV, less than 1 kV, or even less than 100V The average amperage of the electric field can be at least 1 amp, 50 amps, or even at least 100 amps. According to at least some embodiments, the maximum amps can be less than 200 amps, less than 100 amps, less than 50 amps, or less than 10 amps.

The pH adjusted naphthalenic salt of step (a) can further comprise aqueous soluble organic compounds. The soluble organic compounds can be at least 70% oxidized, preferably at least 80% oxidized, more preferably at least 90% oxidized, most preferably at least 98% oxidized.

DETAILED DESCRIPTION OF THE INVENTION

A primary objective of this device is to provide an expandable waste water treatment system which involves a series of module sections in which can be assembled or where sections can be removed to form a waste water treatment system. This system comprises a series of contaminate collection chambers which attach to both ends of a main treatment module(s). The main treatment module(s) houses a preferred electro chemistry method using both ion donating and mixed metal oxide anodes and cathodes. However, the present invention should not be considered, limited or interpreted as merely electro chemistry function performed inside tanks, but where more consideration should be placed on the utility of an expandable assembly utilized for fluid treatment. Other methods such as aeration or chemical dosing can be performed ln the main treatment module(s) where a fluid process may require constant flow while working in tandem with chemical mixing for a pre- or post-treatment of a fluid. The waste water influent slated for treatment can be introduced into the system in continuous flow and where this influent is used as an electrolyte for electrical conductively between an anode and cathode array. Once DC voltage is applied to the array, micro bubbles of hydrogen and oxygen are produced, and once these bubbles generate and release from the anode and cathode arrays, they begin rising up through the water column and attach to contaminate flocculations formed by electro-chemistry reactions. Once contaminates reach the surface, they can be skimmed by a surface skimming device and deposited into either the beginning, center or ending contaminate collection chambers.

Electro-Coagulation is an electrochemistry method used to coagulate wastewater contaminates for ease of separation and collection from the wastewater stream. Wastewater when exposed to a controlled electrical field allows microscopic solids to attract, (like magnetism) forming higher concentrations of solids for greater removal efficiencies.

Selective material types or coatings applied to the anodes and cathodes provide several unique abilities in utilizing half redox ion reactions in which can enhance the fluid treatment process. Mixed Metal Oxidizes, (MMO) typically used are non-donors of ions to the influent and where based on the type of MMO's selected, certain electrochemistry reactions can occur. For example, if combining titanium anodes with ruthenium oxide coated cathodes and if the influent contains salinity, chlorine is evolved which can be used to dis-infect the effluent. The electromagnetic field created by the selected materials used in the electrodes creates hydroxyl and peroxide ions or other reactive oxygen species that can be made more active by rocking, vibrating or shaking the electrodes improving the oxidation by at least 1% and as high as at least 50%.

The electromagnetic field created by electrodes to create hydroxyl and peroxide ions or other reactive oxygen species is made more active by rocking, vibrating or shaking the electrodes. The oxidation is increased by at least 1% and as much as 150% with 170 Hz mechanical vibration and as much as 90% with 45 kHz ultrasonic agitation compared to stationary electrode with no rocking, vibrating or shaking.

Salt removal is only needed if the water has unacceptable salt concentrations. The water must be cooled to less than 70 degrees F., preferably below 50 degrees F. to allow proper operation for the next step—salt removal. The organic materials must be removed to a level of less than 1% prior to salt removal to permit efficient salt removal.

The cooled, organic free water is treated by a technology from ECR Desalination that relies on electro-chemistry techniques for separating salt from salt contaminated water without using costly membranes. This technology has been in commercial scale use starting in 2004 for applications other than producing clean water from salty water up to 9000 gallons per minute. Salt is removed via a special low energy field effect technique producing clean water and solid salts which are then separated. The mechanism for solid salt formation is ionic nucleation which can happen at much lower salt concentrations than conventional crystallization. Sodium chloride crystallizes as 23.5% whereas this process can allow precipitation at less than 1%. The solid salt generated has hydrogen bubbles attached so it will float, a novel approach to making separation easier than having salt settle to the bottom which can lead to plugging and loss of separation. The floating salt is skimmed off, decanted off or filtered off the clean water. So much salt is removed that Water can meet drinking water specification for the United States if needed or to make irrigation or river disposal standards. Once separated, salt can be dried and formed into any size and shape particle for uses in many applications from food, water softening and industrial. Alternatively, the salt can be made into a concentrated brine for other uses requiring a liquid form in water for applications such as fracking. It is well known that some membrane technology costs are about $1.65 (operation and maintenance) per 1,000 gallons of desalinated potable water. ECR has a related cost at a comparable size at about $0.12 per 1,000 gallons of desalinated water. The process runs at constant current of about 30-60 amps at 4-7 volts (voltage varies depending on conductivity of the water and concentration of the water salts, organics and other conductive materials.

Example 1

A 1 weight percent solution of glycerin in deionized water was used to demonstrate the effect of agitation on the oxidation of organic compounds. As the glycerin oxidizes it reacts to form smaller and smaller molecules. Carbon Oxygen Demand (COD) provides a measure of the organic content of the solution. By measuring COD during an oxidation reaction one can track the disappearance of the organic compounds with time and thereby quantify oxidation under different agitation conditions.

For each experiment 450 ml of the glycerin solution were placed in a 500 ml glass beaker. NaCl was added to make a 1 weight percent NaCl solution by weight. The NaCl was necessary for the solution to be electrically conductive. MMO and titanium electrodes, separated by 0.25 inches were inserted into the solution and DC power was established to the electrodes. The voltage was controlled so that current flow between the electrodes was steady at 10 amps. The decrease in COD level of the solutions was determined after 60 minutes.

Experiment 1—no agitation, rocking or vibration, COD reduction 2230 ppm

Experiment 2—beaker placed in ultrasonic bath@45 kHz, COD reduction 4180 ppm

Experiment 3—mechanical vibration of electrodes@200 Hz, COD reduction 5775 ppm

Compared to Experiment 1, oxidation was improved in Experiment 2 by 90%, and in Experiment 3 by 160%.

The combination of the organic removal unit, cooling unit and the salt removal unit is a unique and novel combination allowing for cleanup and reuse of waste from oil production allowing oil recovery, water recycle, salt recycle and potable water production.

Embodiments

1. A process to recover salts of naphthalenic acid from an aqueous stream comprising the steps of:
    a) adjusting the pH of the naphthalenic salts with an aqueous diluent,
    b) optionally adding a hydrocarbon diluent,
    c) treating the naphthalenic soap derivative in aqueous diluent with an electrical field such that the naphthalenic acid coalesces into larger droplets and,
    d) recovering the larger droplets, thereby removing at least 50% of the naphthalenic acid from the oil stream.
    e) oxidizing any soluble forms of the naphthalenic salt or any other organics by hydroxy and peroxide groups or other reactive oxygen species,
    f) formed by an electric field generated by at least one electrode comprising titanium and/or the at least one electrode comprising coatings of ruthenium oxide or iridium oxide or combinations applied to said titanium electrode.
2. The process of claim 1 wherein the aqueous diluent of step (a) has a pH of less than about 4.
3. The process of claim 1 wherein the aqueous diluent of step (a) has a pH of less than about 1
4. Process of claim 1 wherein the aqueous diluent is a mineral acid
5. Process of claim 1 wherein the preferred aqueous diluent is sulfuric acid
6. The process of claim 1 wherein step (a) has an adjusted pH from less than about 8 to more than about 0.01.
7. The process of claim 1 wherein the salt is converted to naphthalenic acid.
8. The process of claim 1 wherein the electrical field of step (f) generates hydrogen gas bubbles which attach to the naphthalenic acid.
9. The process of claim 1 wherein the electric field has a direct current voltage of at least 1 V, 10 V, 100 V, 1 kV, or even at least 20 kV and the electric field has a maximum Voltage of less than 50 kV, less than 30 kV, less than 10 kV, less than 1 kV, or even less than 100 V.
10. The process of claim 1 wherein the electric field has an average amperage of at least 1 amp, 50 amps, or even at least 100 amps and the electric field has a maximum amps of less than 200 amps, less than 100 amps, less than 50 amps, or less than 10 amps.
11. A process to produce water comprising less than 10,000 ppm naphthalenic acid derivatives from an naphthalenic acid-containing emulsion stream comprising the sequential steps of:
    a) adjusting the pH of the naphthalenic salt with a first aqueous diluent,
    b) optionally adding a hydrocarbon diluent,
    c) treating the naphthalenic salt in aqueous diluent with an electrical field such that the naphthalenic salt coalesces into larger droplets and,
    d) recovering the larger droplets, thereby removing at least 50% of the naphthalenic acid from the oil stream.
12. The process of claim 11 wherein the first aqueous diluent of step (a) has a pH of less than about 4.
13. Process of claim 11 wherein the aqueous diluent is a mineral acid.
14. Process of claim 11 wherein the aqueous diluent is sulfuric acid.
15. The process of claim 11 wherein step (c) has an adjusted pH from about 8 to less than about 0.01.
16. The process of claim 11 wherein the electrical field of step (c) generates hydrogen gas bubbles which attach to the naphthalenic acid.
17. The process of claim 11 wherein the electrical field has a direct current voltage of at least 1 V, 10 V, 100 V, 1 kV, or even at least 20 kV and the electric field has a maximum Voltage of less than 50 kV, less than 30 kV, less than 10 kV, less than 1 kV, or even less than 100 V.
18. The process of claim 11 wherein the electric field has an average amperage of at least 1 amp, 50 amps, or even at least 100 amps and the electric field has a maximum amps of less than 200 amps, less than 100 amps, less than 50 amps, or less than 10 amps.
19. The process of claim 18 wherein the naphthalenic salt in the naphthalenic acid containing emulsion stream further comprises aqueous soluble organic compounds.
20. The process of claim 18 wherein the soluble organic compounds are at least 70 weight % oxidized.
21. A process to use an electromagnetic field created by electrodes to create hydroxyl and peroxide ions or other reactive oxygen species that is made more active by rocking, vibrating or shaking the electrodes increasing the oxidation by at least 1% and as high as at least 50% compared to stationary electrodes with no rocking, vibrating or shaking.
22. A process to use an electromagnetic field created by electrodes to create hydroxyl and peroxide ions or other reactive oxygen species that is made more active by rocking, vibrating or shaking the electrodes to keep the electrodes from coating by at least 1% and as high as at least 50% compared to stationary electrodes with no rocking, vibrating or shaking.
23. The process of claim 1 wherein a decanting step is inserted after step (a).
24. The process of claim 11 wherein a decanting step is inserted after step (a).
25. A process to recover naphthalenic acid from an aqueous stream comprising naphthalenic salts, the process comprising the sequential steps of:
    g) adjusting the pH of the naphthalenic salts with an aqueous diluent,
    h) optionally adding a hydrocarbon diluent,
    i) treating the naphthalenic soap derivative in aqueous diluent with an electrical field such that the naphthalenic acid coalesces into droplets, preferably larger droplets than formed without electrical field application, and j) recovering the larger droplets, thereby removing at least 50% of the naphthalenic acid from the oil stream.
k) oxidizing any soluble forms of the naphthalenic salt or any other organics by hydroxy and peroxide groups or other reactive oxygen species,
l) formed by an electric field generated by use of Titanium comprising an electrode and by the use of coatings of ruthenium oxide or iridium oxide or combinations applied to titanium electrodes.

26. The process of claim 25 wherein the aqueous diluent of step (a) has a pH of less than about 4.
27. The process of claim 25 wherein the aqueous diluent of step (a) has a pH of less than about 1.
28. The process of claim 25 wherein the aqueous diluent is a mineral acid
29. The process of claim 25 wherein the preferred aqueous diluent is sulfuric acid
30. The process of claim 25 wherein step (a) has an adjusted pH from less than about 8 to more than about 0.01.
31. The process of claim 25 wherein the salt is converted to naphthalenic acid.
32. The process of claim 25 wherein the electrical field of step (f) generates hydrogen gas bubbles which attach to the naphthalenic acid.
33. The process of claim 25 wherein the electric field has a direct current voltage of at least 1 V, 10 V, 100 V, 1 kV, or even at least 20 kV and the electric field has a maximum Voltage of less than 50 kV, less than 30 kV, less than 10 kV, less than 1 kV, or even less than 100 V.
34. The process of claim 25 wherein the electric field has an average amperage of at least 1 amp, 50 amps, or even at least 100 amps and the electric field has a maximum amps of less than 200 amps, less than 100 amps, less than 50 amps, or less than 10 amps.
35. The process of claim 25 wherein a decanting step is inserted after step a.
36. The process of claim 1 wherein the aqueous diluent stream of step (a) has a pH of less than about 4 and more than about 0.01.
37. The process of claim 11 wherein the aqueous diluent stream of step (a) has a pH of less than about 4 and more than about 0.01.
38. The process of claim 25 wherein the aqueous diluent stream of step (a) has a pH of less than about 4 and more than about 0.01.
39. The process of claim 1 wherein the aqueous diluent stream of step (a) has a pH of less than about 1 and more than about 0.01.
40. The process of claim 11 wherein the aqueous diluent stream of step (a) has a pH of less than about 1 and more than about 0.01.
41. The process of claim 25 wherein the aqueous diluent stream of step (a) has a pH of less than about 1 and more than about 0.01.
42. The process of claim 11 wherein the aqueous diluent of step (a) has a pH of less than about 1.

We claim:
1. A process to recover salts of naphthalenic acid from an aqueous stream comprising the steps of:
a) adjusting the pH of the naphthalenic salts with an aqueous diluent,
b) optionally adding a hydrocarbon diluent,
c) treating the naphthalenic soap derivative in aqueous diluent with an electrical field such that the naphthalenic acid coalesces into larger droplets and,
d) recovering the larger droplets, thereby removing at least 50% of the naphthalenic acid from the oil stream,
e) oxidizing any soluble forms of the naphthalenic salt or any other organics by hydroxy and peroxide groups or other reactive oxygen species,
f) formed by an electric field generated by at least one electrode comprising titanium and/or the at least one electrode comprising coatings of ruthenium oxide or iridium oxide or combinations applied to said titanium electrode.

2. The process of claim 1 wherein the aqueous diluent of step a) has a pH of less than about 4.
3. The process of claim 1 wherein the aqueous diluent is a mineral acid.
4. The process of claim 1 wherein the preferred aqueous diluent is sulfuric acid.
5. The process of claim 1 wherein step a) has an adjusted pH from less than about 8 to more than about 0.01.
6. The process of claim 1 wherein the salt is converted to naphthalenic acid.
7. The process of claim 1 wherein the electrical field of step f) generates hydrogen gas bubbles which attach to the naphthalenic acid.
8. The process of claim 1 wherein the electric field has a direct current voltage of at least 1 V and the electric field has a maximum Voltage of less than 50 kV.
9. The process of claim 1 wherein the electric field has an average amperage of at least 1 amp and the electric field has a maximum amps of less than 200 amps.
10. A process to produce water comprising less than 10,000 ppm naphthalenic acid derivatives from an naphthalenic acid-containing emulsion stream comprising the sequential steps of:
a) adjusting the pH of the naphthalenic salt with a first aqueous diluent,
b) optionally adding a hydrocarbon diluent,
c) treating the naphthalenic salt in aqueous diluent with an electrical field such that the naphthalenic salt coalesces into larger droplets and,
d) recovering the larger droplets, thereby removing at least 50% of the naphthalenic acid from the oil stream.

11. The process of claim 10 wherein the first aqueous diluent of step a) has a pH of less than about 4.
12. Process of claim 10 wherein the aqueous diluent is a mineral acid.
13. Process of claim 10 wherein the aqueous diluent is sulfuric acid.
14. The process of claim 10 wherein step (c) has an adjusted pH from about 8 to less than about 0.01.
15. The process of claim 10 wherein the electrical field of step c) generates hydrogen gas bubbles which attach to the naphthalenic acid.
16. The process of claim 10 wherein the electrical field has a direct current voltage of at least 1 V and the electric field has a maximum Voltage of less than 50 kV.
17. The process of claim 10 wherein the electric field has an average amperage of at least 1 amp and the electric field has a maximum amps of less than 200 amps.
18. The process of claim 10 wherein the naphthalenic salt in the naphthalenic acid containing emulsion stream further comprises aqueous soluble organic compounds.
19. The process of claim 18 wherein the soluble organic compounds are at least 70 weight % oxidized.
20. A process to use an electromagnetic field created by electrodes to create hydroxyl and peroxide ions or other reactive oxygen species that is made more active by rocking, vibrating or shaking the electrodes increasing the oxidation by at least 1% and as high as at least 50% compared to stationary electrodes with no rocking, vibrating or shaking.

21. A process to use an electromagnetic field created by electrodes to create hydroxyl and peroxide ions or other reactive oxygen species that is made more active by rocking, vibrating or shaking the electrodes to keep the electrodes from coating by at least 1% and as high as at least 50% compared to stationary electrodes with no rocking, vibrating or shaking.

22. The process of claim 1 wherein a decanting step is inserted after step (a).

23. The process of claim 10 wherein a decanting step is inserted after step (a).

24. A process to recover naphthalenic acid from an aqueous stream comprising naphthalenic salts, the process comprising the sequential steps of:
   a) adjusting the pH of the naphthalenic salts with an aqueous diluent,
   b) optionally adding a hydrocarbon diluent,
   c) treating the naphthalenic soap derivative in aqueous diluent with an electrical field such that the naphthalenic acid coalesces into larger droplets and,
   d) recovering the larger droplets, thereby removing at least 50% of the naphthalenic acid from the oil stream,
   e) oxidizing any soluble forms of the naphthalenic salt or any other organics by hydroxy and peroxide groups or other reactive oxygen species,
   f) formed by an electric field generated by use of Titanium comprising an electrode and by the use of coatings of ruthenium oxide or iridium oxide or combinations applied to titanium electrodes.

25. The process of claim 24 wherein the aqueous diluent of step a) has a pH of less than about 4.

26. The process of claim 24 wherein the aqueous diluent comprises mineral acid.

27. The process of claim 24 wherein the aqueous diluent comprises sulfuric acid.

28. The process of claim 24 wherein step a) has an adjusted pH from less than about 8 to more than 0.01.

29. The process of claim 24 wherein the salt is converted to naphthalenic acid.

30. The process of claim 24 wherein the electrical field of step f) generates hydrogen gas bubbles which attach to the naphthalenic acid.

31. The process of claim 24 wherein the electric field has a direct current voltage of at least 1 V and the electric field has a maximum Voltage of less than 50 kV.

32. The process of claim 24 wherein the electric field has an average amperage of at least 1 amp and the electric field has a maximum amps of less than 200 amps.

33. The process of claim 24 wherein a decanting step is inserted after step a).

* * * * *